(12) United States Patent
Miller

(10) Patent No.: US 7,442,412 B2
(45) Date of Patent: Oct. 28, 2008

(54) HYDROPHOBIC COATING FOR OXIDE SURFACES

(75) Inventor: Seth A. Miller, Sachse, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 10/826,613

(22) Filed: Apr. 16, 2004

(65) Prior Publication Data

US 2004/0224095 A1 Nov. 11, 2004

Related U.S. Application Data

(60) Provisional application No. 60/468,854, filed on May 8, 2003.

(51) Int. Cl.
*B05D 3/10* (2006.01)
(52) U.S. Cl. .............. 427/248.1; 427/255.11; 427/255.14; 427/255.18; 427/255.21; 427/255.6; 427/333; 427/337; 427/340; 427/407.1; 427/407.2; 427/407.3; 427/409
(58) Field of Classification Search ............. 427/248.1, 427/255.11, 255.14, 255.18, 255.21, 255.6, 427/333, 337, 340, 407.1, 407.2, 407.3, 409
See application file for complete search history.

(56) References Cited

U.S. PATENT DOCUMENTS

| | | | | | |
|---|---|---|---|---|---|
| 4,539,061 | A | * | 9/1985 | Sagiv | 156/278 |
| 5,538,762 | A | * | 7/1996 | Ogawa et al. | 427/503 |
| 6,045,864 | A | * | 4/2000 | Lyons et al. | 427/255.23 |
| 6,291,022 | B1 | * | 9/2001 | Hong et al. | 427/389.7 |
| 6,387,517 | B1 | * | 5/2002 | Belleville et al. | 428/447 |
| 2001/0031364 | A1 | * | 10/2001 | Ogawa et al. | 428/428 |

FOREIGN PATENT DOCUMENTS

| | | | |
|---|---|---|---|
| EP | 484746 | * | 5/1992 |
| EP | 1153740 | * | 11/2001 |
| JP | 06116428 A | | 4/1994 |

* cited by examiner

*Primary Examiner*—Erma Cameron
(74) *Attorney, Agent, or Firm*—Wade J. Brady, III; Frederick J. Telecky, Jr.

(57) ABSTRACT

The disclosure relates to hydrophobic coatings for oxidized surfaces and methods of producing the same. Such coatings may be produced by applying a compound of the general formula $AX_n$ or $A(R^1)_m X_n$ to an oxidized surface followed by a nucleophilic compound of the general formula $DR^2$. The processes may result in a hydrophobic unreactive organic coating that sterically inhibits access to the underlying oxidized surface or reactive groups. In selected embodiments, the hydrophobic coating may form a monolayer.

16 Claims, 1 Drawing Sheet

HYDROPHOBIC COATING FOR OXIDE SURFACES

PRIORITY CLAIM

The present application claims priority under 35 U.S.C. §119(e) to U.S. Provisional Patent Application Ser. No. 60/468,854, filed May 8, 2003 and titled "Method of applying a monolayer to an oxide surface".

FIELD OF THE INVENTION

The present invention relates to hydrophobic coatings for oxide surfaces and methods of producing such coatings. More specifically, it relates to hydrophobic coatings that passivate oxide surfaces.

BACKGROUND

The surface properties of a given material largely determine its interaction with the rest of nature. Most metals and semimetals oxidize spontaneously in air, and the resulting oxide surfaces are highly polar and reactive. They tend to absorb water and volatile organics from the air in a way that is difficult to control outside of a laboratory setting. The result is that properties such as rate of corrosion, surface energy, or adhesion forces can vary greatly from sample to sample and stray far from the ideal for a given application.

One approach to solving this problem is to bond an organic film directly to the oxide surface. This can be performed in a number of ways, and an entire discipline has grown around the area of promoting adhesion to a metal film.

For some applications, greater control over film thickness and morphology is required than can be practiced by bulk technologies. For such systems, the thicknesses and uniformities afforded by conventional approaches fail the minimum specification requirements for the application.

One example of an application that requires strict tolerances for the bonding of organic films to an oxide is stiction control in microelectromechanical systems (MEMS). In MEMS devices, oxidized metal or semimetal surfaces (usually silicon or aluminum oxides) can make contact and adhere through van der Waals, dipole, or capillary forces. Because of the small size of the devices, these forces can often overcome any impulses the systems are capable of producing. However, it is often not practical to coat them directly, because the extreme topography of the devices prevents even coating over the entire device surface.

A currently preferred method for anti-stiction coatings in MEMS devices is the application of a self-limiting monolayer to the active oxide surfaces. Such a coating has the advantage of being of uniform thickness across the device, and thin enough not to perturb the fragile MEMS structures.

Most present solutions to this problem involve the reaction of a discrete silyl ester containing both an organic group directly bound to an activated silicon species, and multiple reactive moieties, to form a monolayer. This solution suffers from several drawbacks, including: the tendency of the organosilicon species to polymerize in solution rather than forming a discrete monolayer; the low vapor pressure of most examples from this class, rendering them difficult to deposit from the vapor phase; the narrow range of commercially available starting materials; and the unknown toxicity of some important members of this class.

Other solutions to this problem include the activation of a surface followed by passivation using organic nucleophiles. Zhu has demonstrated activation of a silicon dioxide surface by chlorine followed by passivation using alcohols. One interesting characteristic of the film created is that it is relatively moisture insensitive, despite the presence of hydrolysable Si—O linkages. It is proposed that the close packing of the organic groups inhibits penetration of water and subsequent hydrolysis of the monolayer. This approach suffers from the need to use corrosive chlorine gas, and is thus ill-suited to manufacturing processes.

Schwartz has approached the problem by depositing a monolayer of zirconium atoms atop of aluminum, followed by passivation of the zirconium monolayer with phenols, carboxylic acids, or phosphonic acids. This method creates a coating that is more thermally robust than carboxylic acids on the native aluminum oxide surface.

SUMMARY

The present invention includes hydrophobic coatings for an oxidized surface and methods of producing such a coating.

In one embodiment, the hydrophobic coating may be produced by reacting an active species with the oxide surface. A nucleophile then displaces said species to form a densely packed layer, precluding further reactions.

In selected embodiments, the hydrophobic surface may be a monolayer, resulting in a very regular surface that may have improved resistance to water.

BRIEF DESCRIPTION OF THE FIGURES

For a more complete understanding of the invention, and for further features and advantages, reference is now made to the following description, taken in conjunction with the accompanying drawings, in which.

DETAILED DESCRIPTION

The present invention relates to hydrophobic coatings for oxidized surfaces and methods of producing such coatings.

The coatings may be applied to surfaces that are already oxidized, or materials may be deliberately oxidized or further oxidized by methods known in the art to render them more suitable for the present methods. Materials suitable for use with the present invention may include any metals, semimetals, transition metals, and ceramics. More specifically, underlying materials may include those used to make semiconductors, MEMS or micromachined devices such as Si, Al, Ag, Cu, Fe, Ta, Hf, Ni, binary compounds such as GaAs or InP, ternary or more complicated compounds, and their oxides.

Figure 1:
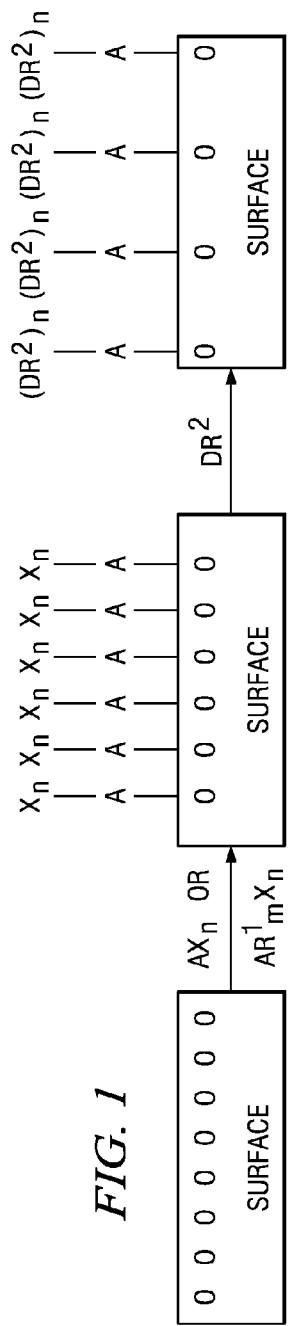
FIG. 1 illustrates a method of coating an oxidized surface with a hydrophobic coating, according to an embodiment of the present invention.

Referring now to FIG. 1, in one method of the present invention an active species, such as one having a general formula $AX_n$ or $A(R^1)_m X_n$ is applied to an oxidized surface to which it covalently bonds. Reactive groups are exposed for further chemistry. A nucleophilic molecule of the general formula $DR^2$ having an unreactive organic substituent $R^2$ is then applied. This nucleophilic molecule reacts with and displaces the exposed reactive groups to become covalently bound. The resulting surface is thus passivated by the nucleophilic group.

In a specific embodiment, A may be any metal, semimetal, transition metal, or ceramic species including but not limited to Si, Zr, Hf, Nb, Ti, Ta, Cu, Ag, and Al, binary compounds such as GaAs or InP, ternary or more complicated compounds, and their oxides. A may be selected based on its ability to form monomeric active species, especially species with sufficient volatility to allow deposition from the vapor phase. X may be any active group, including but not limited to esters, amides such as —N(CH$_3$)$_2$, organic acids such as —OAc, phenolates, thiolates, and phosphonates. R$^1$ maybe any substituent that is inert to the reaction conditions.

The two steps of this process may be carried out at any suitable temperature and pressure and in solution or in a gas phase. In a specific embodiment, a high vacuum system may be used to introduce the active species. Reaction of the nucleophile may be thermodynamically neutral, or nearly so, such that the reaction is driven to completion by flooding the surface with nucleophiles that crowd out those attached to the active species. For example, an alcohol nucleophile will replace a Si or transition metal ester if the nucleophile is provided in large excess.

For some reactions of an exposed reactive group with DR$^2$, a temperature well above ambient temperature may be desirable to drive a reaction to completion, even if it will proceed at ambient temperatures. In some embodiments, use or requirement of a temperature higher than that expected to be encountered in the coating's later environment may result in a more robust coating. If higher than environmental temperatures are needed to create a hydrophobic coating, at lower temperatures sufficient energy will not normally exist to support the reverse reaction, hydrolysis by water.

By choosing appropriate DR$^2$ species, the reaction with the exposed reactive group need not go to completion. While unreacted reactive groups may be capable of reacting with water, steric hindrance from the hydrophobic coating may render them inaccessible.

Figure 2:
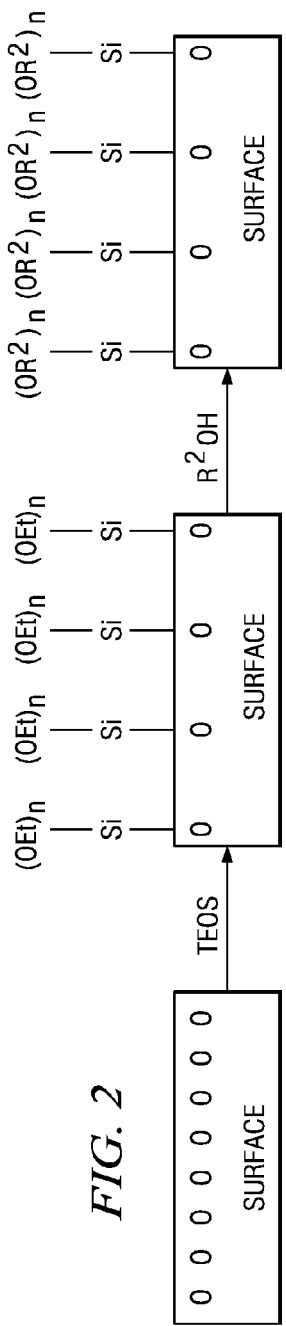
FIG. 2 illustrates a method of coating a SiO$_2$ surface with a hydrophobic coating using TEOS and an alcohol, according to an embodiment of the present invention.

In more specific embodiments SiX$_4$ or Si(R$^1$)$_m$X$_{4-m}$ is applied to the oxidized surface, followed by DR$^2$. Referring now to FIG. 2, in one example of this embodiment, Si(OCH$_2$CH$_3$)$_4$ (TEOS) is applied to an oxidized surface and a long chain organic alcohol is used as the nucleophilic species.

More specifically, TEOS is reacted with an oxide surface, preferably a clean, dry surface, at a temperature from 180-220° C., though not limited to this temperature regime. In a specific embodiment, the reactants may be delivered in the vapor phase under reduced pressure. The reaction of TEOS with the oxide eliminates one to three molecules of ethanol for each TEOS reacted and creates a densely packed surface of ethoxy groups that are then accessible as a new exposed surface. The ethoxy groups may be reacted with any alcohol, which replaces the ethanol to form a new surface in its place. The ethanol released by the reaction process is volatilized and driven away by the heat of the process. As a result of the reaction, a densely packed layer that is inaccessible to water at environmental temperatures results. While unreacted ethoxy groups may remain, the hydrophobic layer renders them inaccessible to water through steric hindrance. Examples of alcohols that can form such a monolayer include decanol, octadecanol, oleyl alcohol, and dodecadienol.

In another specific embodiment, Zr tert-butoxide may be reacted with an oxidized surface near room temperature under ultra-high vacuum, followed by reaction with an alcohol to produce a hydrophobic coating. Examples of alcohols that can form such a monolayer include decanol, octadecanol, oleyl alcohol, and dodecadienol.

Methods of the present invention may be used, in selected embodiments, with existing tools for production of semiconductors, micromachined devices or MEMS. When such tools are used, in many embodiments the reactions will proceed in the gas phase rather than the liquid phase because of compatibility of the tools with gas phase processes. Accordingly, in certain embodiments of the invention, the methods include use of existing toolsets. Modifications of existing toolsets useful to accomplish the methods of the invention will be readily determinable by one of skill in the art.

Figure 3:
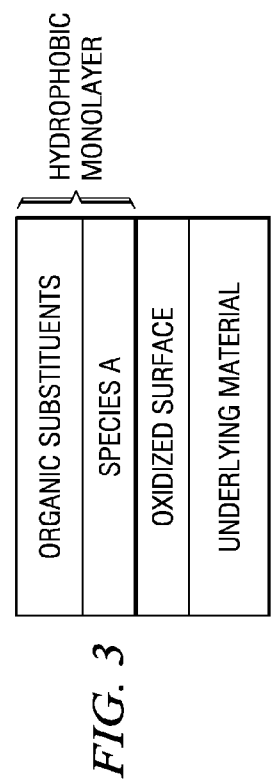
FIG. 3 illustrates a hydrophobic monolayer coating, according to an embodiment of the present invention.

Hydrophobic coatings may be formed by grafting irregular nucleophiles such as polydisperse polymers, so long as steric hindrance and hydrophobicity prevent the entrance of water beneath the outermost surface of the coating. However, in many applications, it will be desirable to form the hydrophobic coatings as a monolayer, such as a self-assembled monolayer, thereby resulting in a more regular hydrophobic surface. For example, as shown in FIG. 3, the initial active species may be reacted with the oxidized surface in such a manner that a monolayer of these species is formed on top of the oxide surface. In some embodiments, atomic layer deposition or other gas-phase deposition of the active transition metal species may facilitate the formation of a monolayer of this species. Similarly, the organic species reacted with the active species may itself form a monolayer. After the reaction, a single monolayer results, providing a very regular hydrophobic coating. This regularity of the coating may increase its robustness in the face of water or hydrophilic molecules in the environment. The uniformity of the surface may also present benefits for application such as MEMS, where the structures are sufficiently small to be influenced by the elevations and depressions likely to be present in a non-monolayer coating.

The formation of a monolayer may be influenced by a variety of factors, including the active species used, the nucleophile used, the conditions under which the active species is reacted with the oxide surface, and the conditions under which the nucleophile is reacted with the active species. Selection of appropriate species and reaction conditions will be readily determinable by one of skill in the art.

Hydrophobic coatings of the present invention may be applied to any oxidized surface. However, in specific embodiments, they may be applied to silica or alumina (oxidized silicon or aluminum) surfaces. More specifically, hydrophobic coatings may be applied to micromachined devices or MEMS.

In an exemplary embodiment, a hydrophobic coating may be applied to the silicon surface contacted by the mirrors of a digital micromirror device (DMD). Application of such a hydrophobic coating to the surface prevents the adherence of water to the surface, as would normally occur when the surface oxidizes. Without water and its attendant intermolecular forces, the mirrors do not adhere to the surface, thereby lengthening the life of the DMD.

Although the present invention has been described in detail, it should be understood that the various changes, substitutions, and alterations could be made hereto without departing from the spirit and scope of the invention as defined by the appended claims.

The invention claimed is:

1. A method of passivating an oxidized surface, comprising the steps of:

applying an active species comprising a compound of a first constituent and a second constituent to the oxidized surface, the first constituent being a metal, semimetal, transition metal, or a ceramic, and the second constituent being a reactive group, so that the first constituent covalently bonds with the oxidized surface and the reactive group is exposed; and then reacting a nucleophilic molecule to displace the exposed reactive group, and to covalently bond the nucleophilic molecule with the first constituent.

2. The method of claim 1, wherein the applying step is performed by vapor phase deposition.

3. The method of claim 1, wherein the compound of the active species further comprises an inert substituent.

4. The method of claim 1, wherein the applying step is performed by a high vacuum system.

5. The method of claim 1, wherein the reacting step comprises flooding the surface with the nucleophilic molecule in excess.

6. The method of claim 1, wherein the reacting step results in a coating in the form of a monolayer.

7. The method of claim 1, wherein the oxidized surface is selected from the group consisting of: metals, semimetals, transition metals, ceramics, alloys thereof, and any combination thereof.

8. The method of claim 1, wherein the second constituent is selected from the group consisting of: esters, amides, organic acids, phenolates, thiolates, phosphonates, alkoxides, and any combinations thereof.

9. The method of claim 1, wherein the nucleophilic molecule is selected from the group consisting of: alcohols, amines, carboxylic acid, phenols, thiols, phosphonic acids, and any combinations thereof.

10. The method of claim 1, wherein the first constituent comprises Si.

11. The method of claim 10, wherein the active species comprises $Si(OCH_2CH_3)_4$ and the nucleophilic molecule comprises an alcohol.

12. The method of claim 11, wherein the alcohol is a long-chain-alcohol.

13. The method of claim 11, wherein the applying step is performed at a temperature from 180° C. to 220° C.

14. The method of claim 13, wherein the applying step is performed by delivering the compound in vapor phase under reduced pressure.

15. The method of claim 11, wherein the second constituent comprises ethoxy groups.

16. The method of claim 1, wherein the reacting step is performed at a temperature above an environmental temperature to which the coating is expected to be exposed.

* * * * *